United States Patent [19]

Bowser et al.

[11] Patent Number: 5,723,112
[45] Date of Patent: Mar. 3, 1998

[54] PYRITHIONE CONTAINING HAIR TREATMENT COMPOSITION

[75] Inventors: Paul Anthony Bowser, Near Bideford; Jonathan David Hague, Wirral; Andrew Malcolm Murray, Parkgate, all of United Kingdom; Ruby Loo Bik Tan-Walker, Chester, Great Britain

[73] Assignee: Chesebrough-Pond's USA Co., Division of Conopco, Inc., Greenwich, Conn.

[21] Appl. No.: 677,259

[22] Filed: Jul. 9, 1996

[30] Foreign Application Priority Data

Jul. 14, 1995 [EP] European Pat. Off. ............ 95304935

[51] Int. Cl.$^6$ ........................ A61K 7/075; A01N 25/04
[52] U.S. Cl. ........................ 424/70.13; 424/70.17; 424/DIG. 4; 514/852; 510/121; 510/123
[58] Field of Search ................ 424/70.1, 70.12, 424/70.27, 70.28, DIG. 4, 70.17, 70.13; 514/852; 510/121, 123, 124, 122

[56] References Cited

U.S. PATENT DOCUMENTS 3,580,853  5/1971  Parran, Jr. ................ 252/152
5,624,666  4/1997  Coffindaffer et al. .

FOREIGN PATENT DOCUMENTS

| 0 093 601 | 11/1983 | European Pat. Off. . |
| 0 136 914 | 4/1985 | European Pat. Off. . |
| 0 173 259 | 3/1986 | European Pat. Off. . |
| 0 530 974 | 3/1993 | European Pat. Off. . |
| 05/194157 | 8/1993 | Japan . |
| WO 95/02389 | 1/1995 | WIPO . |
| WO 95/22311 | 8/1995 | WIPO . |

*Primary Examiner*—Edward J. Webman
*Attorney, Agent, or Firm*—Milton L. Honig

[57] ABSTRACT

The invention provides an antimicrobial hair treatment composition for topical application to human hair in the treatment of, for example, dandruff, including:

(a) at least one surfactant;

(b) fine particles of an insoluble particulate metal pyrithione, in which at least about 90% by weight of the particles have a size of 5 microns or less; and (c) a polymeric, water-soluble cationic deposition aid for the fine particles.

The compositions have good mechanical stability, optical properties and anti-dandruff ability.

8 Claims, No Drawings

PYRITHIONE CONTAINING HAIR TREATMENT COMPOSITION

FIELD OF THE INVENTION

This invention relates to antimicrobial hair treatment compositions for topical application to human hair for the treatment of, for example, dandruff. In particular, the invention relates to an aqueous hair treatment composition comprising a surfactant, water-insoluble antimicrobial particles having a specific particle size distribution and a cationic polymer which serves to enhance the deposition and retention of the particles on the hair and/or the scalp from the composition.

BACKGROUND AND PRIOR ART

Insoluble particulate metal pyrithiones are acknowledged as antimicrobial agents which can be incorporated into antimicrobial compositions, such as antidandruff hair shampoos and conditioners. The zinc salt (hereinafter referred to as ZnPTO) is widely used in this context. Generally, dispersed particles of the ZnPTO are suspended in the composition, which is then applied to the hair to deposit the ZnPTO on the hair and scalp.

A problem encountered with such compositions is that it is difficult to obtain a stable dispersion containing ZnPTO, since its density can lead to separation during storage. Steps taken to prevent separation of the ZnPTO particles have hitherto included restriction of the formulational base to highly viscous emulsions or gels, e.g., by incorporation of thickeners or bulking agents, such as clays or pearlescers, to give structural viscosity to the system and prevent ZnPTO settlement. Such an approach is frequently impractical for shampoo compositions, and can give cloudy, aesthetically-inferior products.

EP-A-0 173 259 describes how this stability problem is particularly acute in the case of fine particulate ZnPTO, which is said to be very sensitive to conditions of liquid media for dispersion, and apt to coagulate in the presence of electrolytes such as salts, shampoo surfactants and cationic polymers. The reference discloses stabilisation of fine particulate ZnPTO in water by means of a specific dispersant, which may include a partly quaternised hydroxyalkylcellulose derivative, or a particular type of copolymeric quaternised cationic polymer blended with at least one inorganic salt. Only suspension stability is discussed; the reference does not address the issue of effective deposition of the ZnPTO active agent onto the hair during use.

By the very nature of the form in which particles of ZnPTO are incorporated into hair treatment compositions, the anti-dandruff benefits attainable are frequently limited, owing to a poor level of deposition of the particles on the intended site, e.g., the hair and/or the scalp, meaning that the majority of the particles remain suspended in the composition and are washed away during rinsing of the composition from the hair.

EP-A-136914 describes an antidandruff hair care composition containing ZnPTO which gives enhanced ZnPTO deposition on the scalp. This is said to be due firstly to the larger particle size of the agglomerates used, at least 20% of which have a size of at least 5 microns, and, secondly, to the absence, in the composition, of "deposition interfering polymeric and clay type suspending agents".

The problems encountered with this approach are, however, that utilisation of large agglomerates of ZnPTO can give rise to difficulties in formulating aesthetically acceptable products. There may also be sensory negatives to the user due to sedimentation of the agglomerates onto the hair in large sticky lumps. Consequently, deposition can be uneven and bioavailability of the active substance to the hair can be reduced, leading to loss of anti-dandruff benefit.

Detergent compositions, for example shampoos, comprising an anionic surfactant, water-insoluble particles and a cationic polymer have been described in U.S. Pat. No. 3,580,853 (Parran). In the detergent compositions described in that patent the cationic polymers are water-soluble cationic nitrogen-containing polymers, in particular quaternary nitrogen substituted cellulose ether derivatives. It appears that the deposition enhancement of the water-insoluble particles derives from the presence of a complex between the anionic surfactant and the cationic polymer which is formed upon dilution of the detergent composition. Washing compositions comprising an anionic surfactant, a water-insoluble particulate substance and a water-soluble cationic polymer which is a non-cellulose cationic polymer are described in EP 93 601.

Neither U.S. Pat. No. 3,580,853 or EP 93 601 contain any specific teachings on the nature or particle size of the particulate substance concerned—this may be an antimicrobial such as ZnPTO and can have a particle diameter ranging anywhere from about 0.2 up to about 50 microns.

It has now been found that antimicrobial hair treatment compositions which have good mechanical stability, and excellent anti-dandruff ability can be obtained by utilising fine particles of insoluble particulate metal pyrithione in combination with a deposition aid.

SUMMARY OF THE INVENTION

Accordingly, in one aspect the present invention provides an antimicrobial hair treatment composition comprising:

(a) at least one surfactant;

(b) fine particles of an insoluble particulate metal pyrithione, in which at least about 90% by weight of the particles have a size of 5 microns or less; and (c) a polymeric water-soluble cationic deposition aid for the fine particles.

DETAILED DESCRIPTION AND PREFERRED EMBODIMENTS

The insoluble particulate metal pyrithione may be represented by the following general formula:

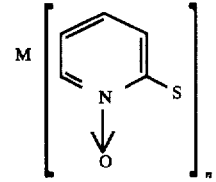

in which M is a polyvalent metal ion and n corresponds to the valency of M.

Preferred examples of M include magnesium, barium, strontium, zinc, cadmium, tin and zirconium. Especially preferred is zinc.

The fine particles of metal pyrithione have a size distribution in which at least about 90% of the particles have a size of 5 microns or less. Preferably, the size distribution is such that at least about 90% of the particles have a size of 1 micron or less. It is thought that this small size enables the antimicrobial particles to be delivered down to the hair follicle, leading to a better efficacy.

Various methods for producing fine particles of metal pyrithione are described, for example, in EP-A-0 173 259.

The amount of metal pyrithione incorporated into the compositions of the invention may depend on the type of composition and the exact nature of the material used. A preferred amount of metal pyrithione is from about 0.001 to about 5% by weight of the total composition, more preferably from about 0.1 to about 3% by weight.

The composition according to the invention comprises at least one surfactant, preferably chosen from anionic, cationic, nonionic, amphoteric and zwitterionic surfactants, and mixtures thereof.

A particularly preferred hair treatment composition in accordance with the invention is a shampoo composition in which at least one surfactant provides a deterging benefit. The deterging surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or diethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 0.1 to 50% by weight, preferably from 0.5 to 30% by weight.

Hair treatment compositions in accordance with the invention may also take the form of hair conditioning compositions, which preferably comprise one or more cationic surfactants. The use of cationic surfactants is especially preferred, because these ingredients are capable of providing conditioning benefits to hair.

Examples of cationic surfactants include:

quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethyammonium hydroxide, hexadecyltrimethylammonium hydroxide, cetyltrimethylammonium hydroxide, octyldimethylbenzylammonium hydroxide, decyldimethylbenzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides Cetylpyridinium hydroxide or salts thereof, e.g., chloride
Quaternium -5
Quaternium -31
Quaternium -18
and mixtures thereof.

In hair conditioning compositions according to the invention, the level of cationic surfactant is preferably from 0.01 to 10%, more preferably 0.05 to 5%, most preferably 0.1 to 2% by weight of the composition.

Hair treatment compositions of the invention may also contain one or more conditioning agents, as are well known in the art. The conditioning agents may include silicones, protein hydrolyzates, quaternised protein hydrolysates and other materials which are known in the art as having desirable hair conditioning properties.

Silicones are the most preferred conditioning agents.

Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution. Alternatively, the high viscosity material may be in the form of an emulsion in water. The emulsion may be of high viscosity oil or of a solution of gum in a lower viscosity oil. The particle size of the oil phase may be anywhere in the range from 30 nanometers to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition. Advantageously, a silicone with a viscosity in the range 1–20 million cst is used. The silicone is preferably emulsion-polymerised, since this enables silicones of very high viscosity to be more easily processed. The silicone can be cross-linked.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

In accordance with the invention, the hair treatment composition contains a polymeric water-soluble cationic deposition aid for the fine particles. By "deposition aid" is meant an agent which enhances deposition of the fine particles of metal pyrithione on the intended site, i.e., the hair and/or the scalp.

The deposition aid will generally be present at levels of from 0.01 to 5%, preferably from about 0.5 to 1%, more preferably from about 0.08% to about 0.5% by weight.

Preferably the cationic charge density of the deposition aid, which is defined as the reciprocal of the molecular weight of a monomeric unit of the polymer containing 1 charge, is at least 0.1 meq/g, preferably above 0.8 or higher. The cationic charge density should not exceed 4 meq/g, it is preferably less than 3 and more preferably less than 2 meq/g. The charge density can be measured using conductimetric analysis and should be within the above limits at the desired pH of use, which will in general be from about 3 to 9 and preferably between 4 and 8.

Preferred deposition aids are cationic derivatives of guar gum and cationic polyacrylamides.

Suitable cationic derivatives of guar gum are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

A particularly preferred deposition aid is Jaguar C13S with a cationic charge density of 0.8 meq/g. Other particularly suitable materials include Jaguar C15, Jaguar C17 and Jaguar C16 and Jaguar C162.

Suitable cationic polyacrylamides are described in WO 95/22311.

The composition may further comprise from 0.1 to 5% of a suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. A further suitable suspending agent is dihydrogenated tallow phthalic acid amide (available from Stepan Chemical Co. under the trademark Stepan TAB-2)

Suitable cross linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into hair treatment compositions of the invention is a fatty alcohol material. The use of these materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

The hair treatment compositions of the invention are preferably aqueous based. The compositions suitably comprise water in amount of from about 20 to about 99% by weight of the total composition.

The compositions of the invention are preferably rinse-off compositions, i.e., suitable for applying to the hair and/or scalp, left thereon for an appropriate period of time and then rinsed off with water. Thus, shampoos are a particularly preferred product form for compositions of the invention.

Depending on the type of composition employed, one or more additional ingredients conventionally incorporated into hair treatment formulations may be included in the compositions of the invention. Such additional ingredients include opacifiers such as polyethylene glycol distearate and ethylene glycol stearates, polymer lattices, additional antimicrobial agents, foam boosters, perfumes, colouring agents, preservatives, viscosity modifiers, proteins, polymers, buffering or pH adjusting agents, moisturising agents, herb or other plant extracts and other natural ingredients.

The invention is further illustrated by way of the following non-limitative examples.

EXAMPLES 1 & 2

Hair shampoo compositions in accordance with the present invention, comprising fine particulate metal pyrithione and a deposition polymer were prepared. The two compositions had the following formulations.

| INGREDIENT | % BY WEIGHT | |
|---|---|---|
| | EXAMPLE 1 | EXAMPLE 2 |
| Sodium lauryl ether sulphate 2EO (28% active) | 50 | 50 |
| Cocamidopropyl betaine (30% active) | 6.7 | 6.7 |
| Jaguar C13S | 0.1 | 0.1 |
| Zinc pyrithione, fine particle size (48% active) | 2.08 | 2.08 |
| CARBOPOL 980 | 0.4 | 0.4 |
| Ethylene glycol monostearate | 3.0 | 3.0 |
| Dimethicone (60% aqueous emulsion) | 3.34 | 1.7 |
| Zinc sulphate heptahydrate | 0.1 | 0.1 |
| Vitamin E acetate | 0.05 | 0.05 |
| Preservative, colour, fragrance | q.s. | |
| Water | to 100% | |

Both shampoos gave excellent anti-dandruff performance on the hair, and were stable without visible signs of separation after three months storage both at room temperature and at 45° C.

EXAMPLE 3

A series of compositions were prepared to test the level of deposition on skin of zinc pyrithione from formulations according to the invention compared with control formulations containing no deposition polymer, and to demonstrate the effect of reducing the particle size of the zinc pyrithione.

| Ingredient | Composition (% wt) | | |
|---|---|---|---|
| | A | B | C |
| Sodium lauryl ether sulphate | 14 | 14 | 14 |
| Cocamidopropylbetaine | 2 | 2 | 2 |
| Dimethicone emulsion[1] | — | 1 | 1 |
| Zinc pyrithione[2] | — | — | 1 |
| Zinc pyrithione[3] | 1 | 1 | — |
| Carbomer | — | 0.6 | 0.6 |
| Guar hydroxypropyl trimonium chloride | — | 0.1 | 0.1 |
| Veegum[4] | 0.6 | — | — |

[1]X2-1766 gum, ex Dow Corning
[2]Zinc pyrithione ex Olin, 90% of particles size less than 1 micron
[3]Zinc pyrithione ex Olin, 90% of particles size less than 5 micron
[4]Colloidal magnesium aluminium silicate, ex R. T. Vanderbilt Each of the above Compositions A to C was subjected to a standard deposition test on skin and the level of zinc pyrithione deposited in each case was measured using the technique of X-ray fluorescence. The methods used are described below:

Panellist Selection

Ten panellists (5 male and 5 female; age 18–60 years) were recruited from volunteers who did not suffer from any skin disorders such as psoriasis or eczema.

Test Procedure

On each inside forearm, six circular areas of diameter 25 mm were marked using ball-point pen. Before product application, one of the circles on each forearm was tape-stripped using J-Clear tape. Pressure was applied to the taped area for 30 seconds using a rubber press. This initial tape strip was used to determine the baseline reading.

a) Calibration

For the calibration test, on each of the remaining area, 20 μl of diluted ZnPTO Fine Particle Size grade *(ex. Olin) was applied and allowed to dry. The final amounts of ZnPTO dosed at each of the sites were 0,1,2,5 and 10 μg/cm2 of ZnPTO. The calibration was then repeated on the other arm.

*(Fine Particle Size grade: 90% of ZnPTO particles have less than 1 micron size).

b) Composition Application

On each of the remaining areas, each composition was applied as follows:

A polythene cylinder of inner diameter 25 mm was placed on the marked circle and pressed to the skin to make a seal. 100 μl of tenfold diluted composition (3 g composition diluted with 27 g distilled water) was applied to the marked area and agitated for 30 seconds using a glass rod. The composition was then rinsed with 2×5 ml of distilled water, directed over the application area using a syringe.

The test compositions were applied to designated sites according to a balanced position allocation to minimise any bias. Replicates were carried out using a repeat design after randomising row positions.

After 15 minutes of drying, each circle was tape-stripped using J-Clear tape. Pressure was applied to each taped area for 30 seconds using a rubber press. Zinc counts on the tape-strips were measured using X-ray fluoresence spectroscopy.

XRF Fluorescence Spectroscopy Analysis of Zinc and Sulphur Content

The tape strips were mounted on aluminium rings and measured for zinc and sulphur using a Philips PW2400 wavelength dispersive X-ray fluorescence spectrometer. The nett zinc counts were obtained by subtracting the counts obtained from blank tape strips from the gross Zinc counts.

The results are shown below in Table 1:

TABLE 1

| Composition | Zinc deposited (Kcounts/s) |
|---|---|
| A | 0.23 |
| B | 0.45 |
| C | 0.63 |

Comparison of the level of zinc deposition from Compositions A and B respectively shows a statistically significant difference, with a confidence level of >99%, in favour of composition B, containing cationic deposition polymer.

Comparison of the level of zinc deposition from Compositions B and C respectively shows a statistically significant difference, with a confidence level of >99%, in favour of composition C, containing smaller particle size zinc pyrithione.

We claim:

1. An antimicrobial hair treatment composition comprising:

(a) from 0.1 to 50% by weight of surfactant;
   (b) from 0.001 to 5% by weight of fine particles of an insoluble particulate metal pyrithione, in which at least about 90% by weight of the particles have a size of 1 microns or less; and
   (c) from 0.01 to 5% by weight of a polymeric, water-soluble cationic deposition aid for the fine particles.

2. A composition according to claim 1 in which metal pyrithione is zinc pyrithione.

3. A composition according to claim 1 in which the metal pyrithione is present in the composition in an amount of from about 0.1 to about 3% by weight.

4. A composition according to claim 1 in which the deposition aid is a cationic derivative of guar gum or a cationic polyacrylamide.

5. A composition according to any preceding claim, which is shampoo composition, in which at least one surfactant is selected from anionic, nonionic, amphoteric and zwitterionic surfactants, and mixtures thereof, in a total amount of from about 0.5 to 30% by weight of the composition.

6. A composition according to claim 1, which further comprises a conditioning agent selected from volatile and non-volatile silicones.

7. A method of treating dandruff comprising applying to the hair an antimicrobial composition comprising:

(a) from 0.1 to 50% by weight of surfactant;
   (b) from 0.001 to 5% by weight of fine particles of an insoluble particulate metal pyrithione, in which at least about 90% by weight of the particles have a size of 1 microns or less; and
   (c) from 0.01 to 5% by weight of a polymeric, water-soluble cationic deposition aid for the fine particles.

8. A composition according to claim 4 wherein the cationic deposition aid is guar hydroxypropyl trimonium chloride.

* * * * *